United States Patent
Sammak et al.

(10) Patent No.: US 7,482,167 B2
(45) Date of Patent: Jan. 27, 2009

(54) MICROBEAD-BASED TEST METHODS FOR FLUORESCENCE IMAGING SYSTEMS

(75) Inventors: Paul Sammak, Pittsburgh, PA (US); Gustavo Rosania, Ann Arbor, MI (US); Lawrence J. Zana, Gibsonia, PA (US); Kim Ippolito, Pittsburgh, PA (US); Jason Bush, Pittsburgh, PA (US); Alex Friedman, Pittsburgh, PA (US); Sarah Burroughs Tencza, Pittsburgh, PA (US); Ravi Kapur, Gibsonia, PA (US)

(73) Assignee: Cellomics, Inc., Pittsburgh, PA (US)

( * ) Notice: Subject to any disclaimer, the term of this patent is extended or adjusted under 35 U.S.C. 154(b) by 834 days.

(21) Appl. No.: 11/078,998

(22) Filed: Mar. 11, 2005

(65) Prior Publication Data

US 2005/0176056 A1  Aug. 11, 2005

Related U.S. Application Data

(62) Division of application No. 09/997,821, filed on Nov. 30, 2001, now Pat. No. 6,905,881.

(60) Provisional application No. 60/250,392, filed on Nov. 30, 2000.

(51) Int. Cl.
 G01N 33/48  (2006.01)
(52) U.S. Cl. .................. 436/164; 422/82.07; 422/82.08
(58) Field of Classification Search ............. 422/82.07, 422/82.08
 See application file for complete search history.

(56) References Cited

U.S. PATENT DOCUMENTS

| | | | |
|---|---|---|---|
| 3,700,305 A * | 10/1972 | Bingham | 359/540 |
| 4,689,307 A * | 8/1987 | Schwartz | 436/8 |
| 4,767,206 A | 8/1988 | Schwartz | |
| 4,774,189 A | 9/1988 | Schwartz | |
| 4,868,126 A | 9/1989 | Schwartz | |
| 4,912,333 A * | 3/1990 | Roberts et al. | 250/487.1 |
| 5,084,394 A | 1/1992 | Vogt et al. | |
| 5,093,234 A | 3/1992 | Schwartz | |
| 5,380,663 A | 1/1995 | Schwartz et al. | |
| 5,786,219 A | 7/1998 | Zhang et al. | |
| 5,989,835 A | 11/1999 | Dunlay et al. | |
| 6,074,879 A | 6/2000 | Zelmanovic et al. | |
| 6,103,479 A | 8/2000 | Taylor | |
| 6,133,436 A | 10/2000 | Köster et al. | |
| 6,232,066 B1 | 5/2001 | Felder et al. | |
| 6,238,869 B1 | 5/2001 | Kris et al. | |

FOREIGN PATENT DOCUMENTS

JP   63036151 A   2/1988

(Continued)

OTHER PUBLICATIONS

Debiasio, et al., (1996), Mol. Biol. Cell., vol. 7, pp. 1259.

(Continued)

Primary Examiner—Lyle A Alexander
(74) Attorney, Agent, or Firm—McDonnell Boehnen Hulbert & Berghoff LLP

(57) ABSTRACT

The present invention provides a test plate and methods for adjusting fluorescence imaging systems involving using a plate with fluorescent microbeads bound to a surface.

19 Claims, 5 Drawing Sheets

Fluorescent Beads as Models for Cells

A. Round Cell

B. Flat Cell

C. Cell-size bead

D. Beads embedded in layer

FOREIGN PATENT DOCUMENTS

| | | |
|---|---|---|
| WO | WO 98/38490 | 9/1998 |
| WO | WO 98/55026 | 12/1998 |

OTHER PUBLICATIONS

Farkas, et al., (1993), Ann. Rev. Physiol., vol. 55, pp. 785-817.
Giuliano and Taylor (1995), Curr. Op. Cell Biol., vol. 7, pp. 4-12.
Guiliano, et al., (1990) Optical Microscopy for Biology, pp. 543-557.
Guiliano, et al., (1995) Ann. Rev. Biophys. Biomol. Struct., vol. 24, pp. 405-434.
Hahn, et al., (1992), Nature, vol. 359, pp. 736-738.
Heim and Tsien, (1996) Curr. Biol., vol. 6 pp. 178-182.
Waggoner, et al., (1996), Hum. Pathol., vol. 27, pp. 494-502.

* cited by examiner

Fluorescent Beads as Models for Cells

A. Round Cell

B. Flat Cell

C. Cell-size bead

D. Beads embedded in layer

Fluorescent Beads and Polymer Layers

Side View  Top View

A. Beads attached to substrate

B. Beads embedded in a polymer layer

F. Two sizes of beads in polymer layer

C. Film in a polymer layer

D. Detached beads in a polymer layer

G. Beads in polymer layer islands

E. Beads in polymer layer islands (a)

(b)

MICROBEAD-BASED TEST METHODS FOR FLUORESCENCE IMAGING SYSTEMS

CROSS REFERENCE

This application is a divisional application of U.S. patent application Ser. No. 09/997,821 filed Nov. 30, 2001, now U.S. Pat. No. 6,905,881 which claims priority to U.S. Provisional Application Ser. No. 60/250,392 filed Nov. 30, 2000.

FIELD OF THE INVENTION

The invention relates to the field of cell-based imaging.

BACKGROUND

High-content screening ("HCS") has been developed to address the need for more detailed information about the temporal-spatial dynamics of cell constituents and processes, and plays an important role in the use of cell-based screening for identification and validation of drug candidates. High-content screens automate the extraction of fluorescence information derived from specific fluorescence-based reagents incorporated into cells attached to a substrate (Giuliano and Taylor (1995), *Curr. Op. Cell Biol.* 7:4; Giuliano et al. (1995) *Ann. Rev. Biophys. Biomol. Struct.* 24:405). Cells are analyzed using an imaging system that can measure spatial as well as temporal dynamics. (Farkas et al. (1993) *Ann. Rev. Physiol.* 55:785; Giuliano et al. (1990) In *Optical Microscopy for Biology*. B. Herman and K. Jacobson (eds.), pp. 543-557. Wiley-Liss, New York; Hahn et al (1992) *Nature* 359:736; Waggoner et al. (1996) *Hum. Pathol.* 27:494). The concept is to treat each cell as a "well" that has spatial and temporal information on the activities of the labeled constituents.

High-content screens can be performed on either fixed cells, using fluorescently labeled antibodies, biological ligands, and/or nucleic acid hybridization probes, or live cells using multicolor fluorescent indicators and "biosensors." The choice of fixed or live cell screens depends on the specific cell-based assay required. The types of biochemical and molecular information now accessible through fluorescence-based reagents applied to cells include ion concentrations, membrane potential, specific translocations, enzyme activities, gene expression, as well as the presence, amounts and patterns of metabolites, proteins, lipids, carbohydrates, and nucleic acid sequences (WO 98/38490; DeBiasio et al., (1996) *Mol. Biol. Cell.* 7:1259; Giuliano et al., (1995) *Ann. Rev. Biophys. Biomol. Struct.* 24:405; Heim and Tsien, (1996) *Curr. Biol.* 6:178).

It is important that local differences in the imaging system and software associated with the optics, illumination, geometry of the plate, or other assay-specific parameters, be minimized to ensure reproducibility and value of the information derived from performing HCS.

Currently, there are no tools designed for diagnostics, calibration, or software validation of fluorescence imaging systems that carry out image-based microscopic measurements and analysis. Such a tool is valuable for HCS assays performed on physically attached cells or objects, as well as for general biological research microscopes, defect identification imaging systems (such as polarization microscopes), industrial or commercial particle counting imaging systems (such as particle counters for explosives detection, and spore and pollen detection.

Previous calibration tools have generally been adapted for use with flow cytometers, such as those using suspensions of fluorescent microbeads to calibrate the illumination, alignment, optics and fluidics of the flow cytometer. Other methods have involved the use of uniform fluorescent films. However, such methods only provide information about fluorescent intensity, and provide no information about size, shape, or spatial distribution of the fluorescent signal, and thus do not permit calibration of an imaging system for these types of parameters.

Thus, the existence of a tool that contains spatial information for diagnostics, calibration, or software validation for verifying image analysis and integrated system accuracy and reproducibility is needed in the art. Instrument calibration is especially important in live cell applications, since slight differences in illumination can have a tremendous impact in the performance of the assay, due to phototoxicity and other issues. An easy-to-use tool for diagnostics, calibration, or software validation would also allow instrument testing prior to each run with automated protocols, and normalization for variability in hardware or software.

A tool in which fluorescent microbeads are bound to a surface would allow absolute reproducibility regarding the actual objects being imaged, such as size, shape, and spatial distribution, as well as the exact position on the test plate on which the objects are imaged (X, Y and Z coordinates). Such a tool would be useful for 1) calibrating imaging systems by measuring known input parameters and adjusting the system to normalize or rescale resulting output data; 2) diagnosing whether system operation is within specifications and to solve problems if performance is out of specifications by testing system sub-components; and 3) testing integrated system performance by determining the veracity of output with known input.

SUMMARY OF THE INVENTION

The present invention fulfills the need in the art for a tool for diagnostics, calibration, or software validation for fluorescence imaging systems. In one aspect, the present invention provides a test plate for fluorescence imaging systems comprising a surface comprising at least a first chemical group, fluorescent microbeads that comprise at least a second chemical group that is bound to the at least first chemical group on the surface and a polymeric layer in which the fluorescent microbeads are embedded.

In another aspect, the invention provides methods for preparing a test plate for fluorescence imaging systems, comprising providing a surface comprising at least a first chemical group, providing fluorescent microbeads comprising at least a second chemical group that is capable of binding to the first chemical group, contacting the surface with the fluorescent microbeads under conditions to permit binding of the at least first chemical group and the at least second chemical group, and adding a polymeric layer to the surface.

In another aspect, the invention provides methods for diagnosing, calibrating, or validating the software of a fluorescence imaging system comprising providing a test plate with fluorescent microbeads bound to a surface of the test plate, acquiring fluorescent images from the fluorescent microbeads, making measurements of one or more properties of the fluorescent images, comparing the measurements to a known value, and adjusting the fluorescence imaging system based on comparing measurements to a known value.

DETAILED DESCRIPTION OF THE INVENTION

In one aspect, the present invention discloses a test plate for fluorescence imaging systems comprising (a) a surface comprising at least a first chemical group for covalent coupling and (b) fluorescent microbeads, wherein the fluorescent microbeads comprise at least a second chemical group that is covalently coupled to the at least first chemical group on the surface.

Figure 1:
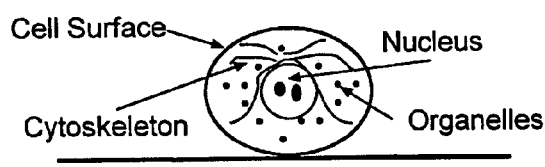
FIG. 1 A-D is a pictorial representation of fluorescent microbeads as models for cells.
Figure 1:
Figure 1:
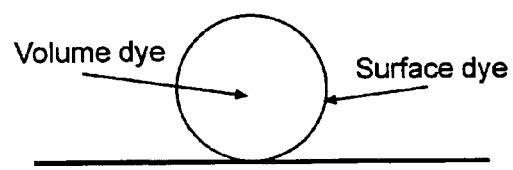
Figure 1:
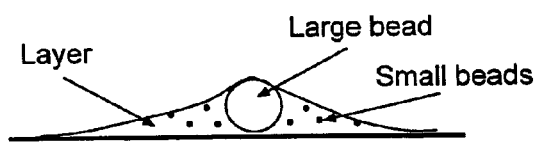

The fluorescent microbeads on the surface serve as surrogates for cells possessing fluorescent reporter molecules (FIG. 1), but with constant and reproducible fluorescent properties that can be measured and used to adjust the parameters of a fluorescence imaging system for better reproducibility and accuracy of results in cell-based screening assays, particularly for high content screening assays.

Microbeads that are similar in size to cell bodies provide a simple models of cells. FIG. 1A shows that cells are bounded by a membrane at the cell surface (10 to 20 micrometer diameter) and contain various structures including the nucleus (5-10 micrometers), globular organelles (about 1 micrometer) and a fibrous cytoskeleton. These structures are fluorescently labeled for cell-based assays. Image-based measurements of intensity, position and distribution indicate cellular responses to drugs and other stimuli. FIG. 1B shows cells that are attached by strong surface contacts to the underlying substrate, and which tend to flatten out.

FIG. 1C shows how fluorophore-labeled microbeads can be used as models for cellular structures, providing advantages for diagnostics, calibration, or software validation including uniformity of size and intensity, and stability over time and location. In addition, the distribution of microbeads can be made more uniform than cells, which tend to move over time.

FIG. 1D shows that microbead-based models of cells can contain multiple components, including microbeads of different sizes and colors, and embedding layers that serve to hold microbeads in place and provide a fluorescent surround. In this example, microbeads of one color and size mimic cell nuclei, smaller microbeads of a second color mimic cell organelles and an embedding layer doped with an additional color fluorophore embed the microbeads and mimic the cell body of flat cells.

Thus, the test plate of the invention can be used to perform any automated diagnostic, calibration or validation test of hardware and software intended to enable a fluorescence imaging system to operate at optimal performance level for the specific cell-based assay that a user might wish to run. "Software validation," as used herein, means any means to determine that the fluorescence imaging software is functioning as intended and/or expected. The software may be instrument-operating software or software for conducting cell screening assays.

As used herein, "fluorescence imaging system" means any instrument, and any associated software and/or fluid handling system, with microscopic/sub-microscopic object detection capabilities used to generate and/or analyze images of fluorescent samples that are fixed to a surface, including fluorescent plate readers. "Images," as used herein, means two-dimensional spatial or temporal maps of fluorescent sample intensities.

As used herein, "high content screening" or "HCS" means any automated optical technique used to detect or measure one or more signals arising from individual cells that are organized in arrays on a surface or in a multi-well plate where the signal from each individual cell in the array is measured separately at one or more time points.

The surface can be any surface that can be used for fluorescence imaging in combination with a fluorescence imaging system. In a preferred embodiment, the surface complies with the standards for calibration plates set forth by the Society of Biomolecular Screening. The surface can be clear polystyrene, glass, or quartz, such as standard microplates of any well number, but can also be made of any other material providing suitable optical properties, as discussed above. Alternately, opaque, non-optical surfaces are suitable if the fluorescent microbeads are attached to the surface on the side towards the illumination and light collection from the sample. The test plate may additionally comprise other materials, such as a rigid plastic, provided that those materials are not part of the surface being imaged. The test plate can be of any size adapted for use in a fluorescence imaging system.

While the first chemical group can be any chemical group that can be covalently coupled to the second chemical group on the fluorescent microbead, it is preferred that the first chemical group of the surface is a reactive amine group. "Amine group," as used herein, refers to any chemical group possessing a free amine moiety, i.e. $R—NH_2$, including, but not limited to, small molecules, polyamino acids, and proteins.

Such amine groups include, but are not limited to, those present in collagen I, bovine serum albumin, fibronectin, laminin, fragments thereof, or organosilanes. In a most preferred embodiment, organosilanes with sulfhydryl or amino groups, collagen I, or bovine serum albumin-coated plates are used.

The use of organosilane or related small molecule chemistries for coupling the bead to the wells provides increased stability over protein based coupling, which is subject to radiation and hydrolysis degradation over time, and provides the means to pattern the beads on the surface. Furthermore, the monolayer self-assembly of organosilanes, provides a homogenous (i.e.: similar number of objects per unit area from field to field) distribution of the coupling chemistry, with controlled density of bonds per unit area, which translates to a uniform distribution of the beads.

In a further embodiment, the surface comprises wells, including, but not limited to, the wells of a standard 96, 384, or 1024 well plate. As defined herein, the term "wells" describes discrete and isolated subsections of the surface, and does not require any depth (see, for example, U.S. Pat. No. 6,103,479). In a more preferred embodiment, the first chemical group is present in the wells on the surface, but not on other portions of the surface.

As used herein, "fluorescent microbeads" or "microbeads" means any microscopically sized beads, preferably spherically shaped, containing or attached to at least one fluorophore. The microbeads can be made of any material that can contain or be attached to a fluorophore, such as glass, ceramic, metal, organic and inorganic polymers (such as plastic and protein-based microbeads), as well as composites thereof. In a preferred embodiment, the microbead is made of glass or plastic.

The fluorophores may be placed within a bead (so that the bead "contains" the fluorophore) or may be attached to the bead via any suitable chemical coupling by methods known in the art. Microbeads containing fluorophores may be prepared by incorporating dyes in the polymerization process of the microbeads. For example, polystyrene microbeads are created from styrene monomers in non-aqueous, low polarity solvents; in this example, hydrophobic dyes would be appropriate. Microbeads containing fluorophores can also be prepared by covalently attaching one or more types of fluorophores to the polymer monomers to control dye concentration, or a soluble dye might be trapped within the bead during polymerization of the microbead from monomer subunits. In a further alternative, a fixed molar ratio of dye can be produced by mixing two monomers in defined ratios, one containing a covalently linked fluorophore.

In a preferred embodiment, the fluorophore is contained within the microbead in order to minimize exposure to the surrounding environment. Such fluorescent microbeads are available commercially (such as from Molecular Probes, Eugene, Oreg.)

The microbeads are fluorescent, with spectra that preferably match the standard fluorescence imaging system-supported dye excitation and emission wavelengths (including Hoescht, FITC, TRITC and Cy5), with minimal cross-talk between different channels (for example, Fluoresbrite™ Bright Blue carboxylate microspheres, Catalog #19103). The fluorescent microbeads on a given plate may all contain or be attached to identical fluorophores, or the plate may contain a mixture of microbeads that contain or are attached to different fluorophores. While it is usually preferable that a single microbead contains a single type of fluorophore, it is also possible to use microbeads that individually contain or are attached to two or more types (colors) of fluorophores to determine, for example, the co-localization of microbeads in two different channels.

The fluorescent microbeads to be used on a given test plate are generally of uniform sizes, although certain applications may make the use of different microbead sizes preferable. As used herein, "uniform size" means having between 0% and 5% size variation, and preferably <1% size variation. The microbeads may include, but are not limited to, those having a size range of between 0.1-50 micrometers in diameter, and more preferably between 0.1 and 20 micrometers in diameter. It is preferred that the microbead size selected for use with a particular fluorescence imaging system be within a usable range as determined by the combination of camera pixel size and objective magnification. In a non-limiting example, for a high-content screening system with a 10× objective in which the beads are used as a model of a nucleus, the fluorescent microbead size is preferably between 4 µm and 10 µm in diameter.

Fluorescent microbeads of between 0.1-2 µm can be viewed at low resolution, without identification of the beads as individual objects, using 10×-20× objectives. In order to identify such beads as individual objects, an objective of 40× or greater should be used. In some cases (i.e.: sub 1 µm beads), an oil immersion objective may be required to resolve individual objects, which will decrease the overall speed of any assays using the test plate. Fluorescent beads up to 50 µm can be used to model whole cells. The largest such beads may be more difficult to bind to the plate, and are somewhat more difficult to focus on, but can be used with the test plate of the invention. It is further preferred that for testing cell-based assays the microbead size be similar to the dimensions of subcellular structures, including small vesicles less than 1 micrometer in diameter and whole nuclei, approximately 10 micrometers in diameter. Larger size microbeads may be used for calibrating objects the size of an entire cell body. The fluorescent microbeads preferably have predictable photobleaching properties, such that they exhibit <50% drop in fluorescence during 60 minutes of continuous illumination using a filter set appropriate for the fluorescent microbeads. Ideally, the fluorescent microbeads are completely stable to photobleaching. Microbead fluorescence is preferably of a uniform fluorescence intensity.

It is further preferred that the microbead fluorescence intensity is such that a 0.5 second integration leads to nearly 100% saturation of the CCD camera of a standard ASII instrument (ADU values of 3800 to 4000 in standard scanning mode), under the appropriate filter set for each microbead type.

Fluorophores that would be favored include rhodamine (red), because of its relative insensitivity to its environment. Fluorescent microbeads are compared to each other from sample to sample and over time, and those that are not susceptible to environmental change, photo damage, oxidative damage or chemical degradation, are desirable. Blue (coumarin) dyes, as well as microbeads labeled with the Alexa™ family of dyes (green to far red, Molecular Probes), are also favored. The specific fluorophore used is generally less important than its broad match to the filter sets used for various assays.

The fluorescent microbead surface comprises a chemical group ("the second chemical group") for covalent or other chemical modifications that are compatible with lab plasticware, dye and microbead chemistry, without creasing, degrading, or distorting lab plasticware, microbead fluorescence, or microbead morphology. Preferred second chemical groups include carboxylate groups, electrophiles such as maleoamido or tresylate, or nucleophiles such as sulfhydryl, amines, or hydroxyl groups, on the surface of fluorescent microbeads. In a more preferred embodiment, the second chemical group comprises a carboxylate group. As used herein, the term "carboxylate group" refers to any chemical moiety containing a free carboxylic acid. In a preferred embodiment, fluorescent microbeads containing carboxylate groups are covalently coupled to an amine-containing surface.

Additionally, the fluorescent microbeads can possess further chemical groups for covalent or other modifications in addition to the second chemical group used for binding to the surface. Such further modifications provide, for example, optimal polarity or hydrophobicity of the fluorescent microbead, to further control coupling to the surface, to provide aqueous solubility, or to provide further chemical stability. Microbead attachment can be mediated by the use of other moieties including sulfates to increase hydrophobicity, aldehydes for covalent reactions with proteins or other amines, and amines for chemical cross linking with bi-functional cross linkers, which allows further bead modifications such as the binding of an additional fluorophore limited to the bead surface.

It is further preferred that the test plate be dry, such as would be achieved by air-drying the plate after its production (see below). While test plates on which the microbeads are strongly bound to the surface can be stored wet for long periods of time, dried plates are more easily transported, and can be stored at least several months at various temperatures, including 4° C. and room temperature. Dried test plates have additional advantages, including the ability to be coated with non-aqueous polymers to improve mechanical, chemical, and optical stability. Dried microbead plates can be rehydrated by adding water or a desired buffer such as PBS or HBSS, with or without additional fluorophores in solution. Such stored microbead plates are hydratable with minimal degradation, distortion or unpredictable alteration of optical/fluorescence properties. The attached fluorescent microbeads on such dried plates withstand fluid shear stresses during addition of liquid, and can therefore be used to test pipettor functionality such as accuracy and precision of pipetting volume, stability of the optics during and after pipetting, mixing of fluid after pipetting, and fluid shear forces exerted while pipetting. Microbeads in aqueous saline buffers (PBS) should be stable for more than one month after rehydration.

In a preferred embodiment of the of the invention, the fluorescent microbeads are embedded in a polymeric layer that excludes oxygen and water, provides physical protection, and minimizes degradation, distortion, or other alterations of the fluorescent properties of the microbeads.

In this embodiment of the invention, the fluorescent microbeads are bound to the surface by any means that provides suitable binding to the surface such that fluorescent microbeads are not disturbed upon polymeric embedding.

The term "binding" or "bound" as used herein refers to chemical interactions including, but not limited to, covalent coupling, ionic (electrostatic) interactions, van der Waals forces, dipole-dipole interactions, and hydrogen bonds. Thus, the first and second chemical groups can be any chemical moieties capable of promoting one of these types of binding. For example, sulfation, carboxylation, or amidation promote microbead binding to various substrates by increasing the enthalpic or entropic binding energy to defined surfaces.

In a preferred embodiment, the fluorescent microbeads are covalently bonded to the surface, as described above.

As used herein, the term "embedded" means encased within a polymeric layer. The polymeric layer can be deposited in a number of different formats (FIG. 2B-G), including a layer with a thickness similar to the microbeads but unrestricted laterally. The polymeric layer may be contained within defined areas such as wells in a plate. Polymeric layer thickness may be microscopically thin, less than the dimensions of the beads, or thicker than the beads. The polymeric layer could be a spot just larger than the microbead. Microbeads of different size and color can be combined within one polymeric layer, and the polymeric layer may or may not itself be doped with fluorophore of a color distinct from the microbeads. The polymeric layer improves the reproducibility and stability of fluorescent microbead with externally attached fluorophores by providing necessary protection from the environment. This protection against environmentally induced changes enables the fluorescent microbeads of the present invention to be compared to each other from sample to sample and over time. Such a polymeric layer also provides a substrate for fluorescent dyes that differ from the microbead in intensity or in color, thus increasing the types of tests enabled by the test plate. (See FIG. 2B) A two component fluorescent sample is useful for measuring relative fluorescence intensity (microbead vs. fluorescent surround). The fluorescent material of the polymeric layer may comprise a fluorescent concentration standard used to calibrate the intensity of the microbeads. The fluorescent material of the polymeric layers may have different spectral characteristics from the microbeads and serve as a multispectral test for filter settings or for calibrating multi-channel cell-based assays.

Figure 2:
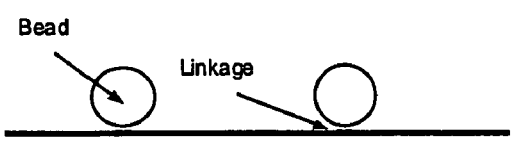
FIG. 2 A-G is a pictorial representation of fluorescent microbeads and polymer layers.
Figure 2:
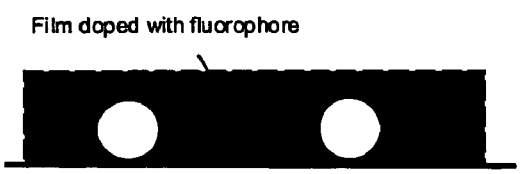
Figure 2:
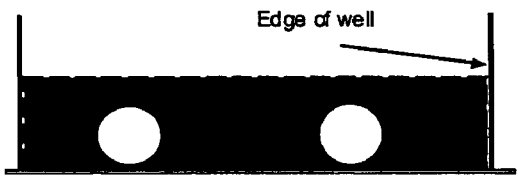
Figure 2:
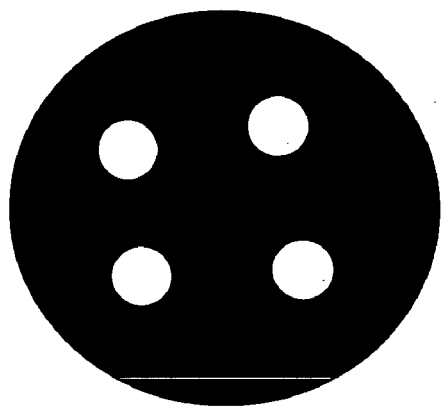
Figure 2:
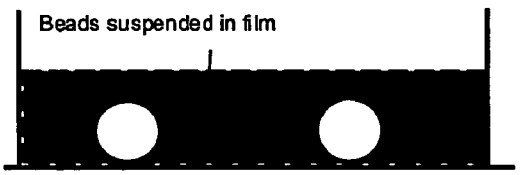
Figure 2:
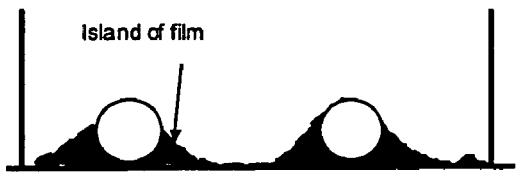
Figure 2:
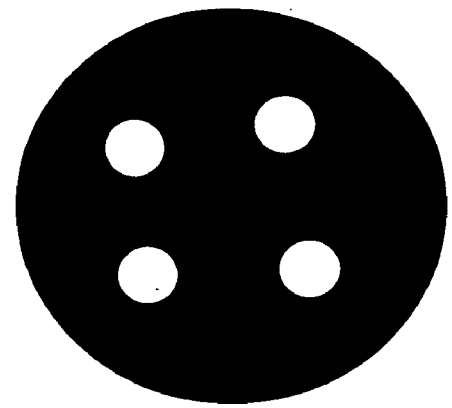

Alternatively, small droplets or islands of a polymeric layer (with or without fluorescent doping) could be deposited surrounding each fluorescent microbead by first applying a low viscosity fluorescent solution and then draining excess solution off of the substrate, leaving small cell-sized droplets surrounding the beads. Such droplets would mimic cell cytoplasm surrounding microbeads that mimic nuclei. (FIGS. 2E and G)

It is preferred that such a polymeric layer be at least partially gas impermeable to reduce oxygen-dependent photobleaching of fluorophores. In an even more preferred embodiment, the polymeric layer comprises components selected from the group consisting of urethane, acrylic, vinyl alcohol, siloxanes, glycols, and epoxy resins.

Desirable characteristics of the polymeric layer include optical clarity, low light scattering, and low-autofluorescence. A desired characteristic of the solvents used to prepare the polymeric layer is chemical compatibility with the microbeads and surface of the plate.

Acrylic polymers use water as solvents, and partial drydown hardens the polymer film into a relatively rigid matrix with good mechanical stability, some gas impermeability, and high optical clarity. Organic solvent-based polymers such as polyurethane have high mechanical stability, gas impermeability, optical clarity, and low background fluorescence. Shellac and resin-based varnishes have good mechanical and chemical stability, but some solvents may dissolve the microbeads, and some resins have high background fluorescence. Epoxy resins are another class of chemically induced polymers that have good mechanical and optical characteristics. However, chemical stability of the microbeads should be matched to the epoxy reactants. Hydrogels, such as polyethylene glycol based polymers, offer chemical compatibility (ethanol or methanol based reactions), with desired optical properties of low auto-fluorescence, scattering and optical clarity. Silicon elastomers, such as polydimethylsiloxane, provide mechanically robust, oxygen impermeable, and optically clear thin films.

In a most preferred embodiment, the polymeric layer comprises a polymer selected from the group consisting of polyurethane, polyacrylate, polysilicones, polyglycols, and polyvinyl alcohols. In a preferred embodiment, the polymeric layer is contained within the wells of the test plate.

Fluorescent microbeads in these polymeric environments are stable for at least one year at temperatures ranging from $-20°$ C. to above $50°$ C.

In another aspect, the present invention provides a method of preparing a test plate for fluorescence imaging systems, comprising:

a) providing a surface comprising at least a first chemical group;

b) providing fluorescent microbeads in a binding buffer, wherein the fluorescent microbeads comprise at least a second chemical group that is capable of binding to the first chemical group; and c) contacting the surface with the fluorescent microbeads under conditions to permit covalent coupling of the at least first chemical group and the at least second chemical group.

In a preferred embodiment, the method further comprises adding a polymeric layer to the surface. In a further preferred embodiment, the polymeric layer is selected from the group consisting of polyurethane, polyacrylate, polysilicones, polyglycols, and polyvinyl alcohol, wherein the fluorescent microbeads are embedded in the polymeric layer. In this aspect, the surface and the fluorescent microbeads are as disclosed above.

As used herein, the term "contacting" means any method by which the fluorescent microbeads are physically placed on the surface under conditions to permit binding. As used herein, the phrase "conditions to permit binding" means any conditions that enables such a chemical interaction to occur.

In a preferred embodiment, the chemical interaction is covalent coupling. The term "covalent coupling" as used herein refers to the chemical reaction between the first chemical group of the surface and the second chemical group of the fluorescent microbeads, as described above. Preferred embodiments of the first and second chemical groups are as disclosed above.

In a preferred embodiment, the binding buffer contains water soluble, 1-ethyl-3-(3-dimethylaminopropyl)carbodiimide (EDAC; can be purchased from Molecular Probes, Catalog # E-2247) and water soluble N-hydroxysulfosuccinimide (NHSS; can be purchased from Molecular Probes, Catalog # H-2249) as activators. Alternatively, the binding buffer may contain 1-ethyl-3-(3-dimethylaminopropyl)carbodiimide hydrochloride (EDC; can be purchased from Pierce Chemical Company) and N-hydroxysuccinimide (sulfo-NHS; can be purchased from Pierce Chemical Company).

The binding buffer to be used in the present invention comprises a buffer solution such as PBS or HBSS buffer, preferably at pH 7, containing EDAC and NHSS. It is preferable that the activators be in an equimolar ratio or in a ratio such that the NHSS is in a 1 to 2.5 fold excess. It is additionally preferable that the EDAC have a concentration of 1-2 mM and the NHSS have a concentration of 1-5 mM. In a most preferred embodiment, the activators are in excess of the concentration of the chemical groups of the microbeads. The minimal effective concentration of alternate activators may be determined by a method similar to that described in the examples below.

Alternately, it is preferred that the binding buffer is acidic in order to promote activation of the carboxylate moieties of the microbeads and the stability of the microbead-activator linkage. Suitable buffers include, but are not limited to citrate, phosphate, acetate, MES, combinations thereof, or any buffer that does not contain an amine moiety. In general, any buffer is acceptable provided that it does not comprise the same chemical moiety as the first chemical group of the surface of the test plate.

Fluorescent microbead suspensions in binding buffer should be unaggregated. It should be possible to disaggregate them by sonication, such that >95% of the microbead population should be single microbeads following sonication. The microbeads are preferably be of greater density than the binding buffer, and it is preferably possible to reversibly centrifuge them through a 10 ml solution by spinning 10 minutes at 1500 rpm, in 15 ml conical tubes, on a standard table top centrifuge.

It is further preferred that the concentration of fluorescent microbeads in binding buffer be in the range of 50,000-2,000,000 microbeads per milliliter. It is further preferred that each well contain between 5,000-200,000 microbeads.

When the density of the microbeads is greater than the density of the buffer, the microbeads usually settle to the plate surface, depending on bead size. In a preferred embodiment, activated carboxylate groups on the surface of the microbeads encounter the free amines on the collagen or BSA film on the surface of the plates and react to form covalent chemical bonds. In addition, the carboxylate and amine containing side chains on any protein molecules on the surface (such as collagen or BSA) react with each other, to form a covalently-crosslinked mesh. It is preferred that the activators be washed away from the microbeads prior to contacting the surface with the microbeads to minimize the competition of the carboxylate groups of the microbeads with the carboxylate groups of the protein for the amine groups of the surface. It is further preferred that the coupling reaction be allowed to proceed for 1 to 4 hours. Subsequently, it is preferred that the buffer be aspirated off and the remaining liquid dried, without altering the position of the microbeads on the plate, in order to maximize the number of microbeads bound to the surface.

Alternatively, the plates may be contacted with the fluorescent microbeads and centrifuged for about 30 minutes at about 1000×g, prior to the incubation period after which the buffer can be aspirated off, and the remaining liquid is preferably dried, such as by air drying for between 1-24 hours, or in a fume hood. This method is especially preferred for use with smaller beads that might not settle to the surface by gravity.

It is preferred that a homogenous microbead distribution is obtained in the wells of a test plate. Such a homogenous microbead distribution is preferably achieved by contacting microbeads to each well in a volume of between about 100-300 µl.

In a preferred embodiment, the method further comprises embedding the microbeads in a polymeric layer as discussed above. It is preferred that the surface be dried prior to application of the polymeric layer. It is further preferred that an aliquot of the selected polymer be added to each well of the test plate. If the polymer is too viscous, it may be diluted with petroleum ethers or other organic based solvents. The test plate is then left to air-dry to facilitate polymerization.

In another aspect, the invention discloses a method for testing a fluorescence imaging system. In one embodiment of this aspect of the invention, the method comprises providing a test plate with fluorescent microbeads fixed on a surface of the test plate, acquiring fluorescent images from the fluorescent microbeads, making a measurement of one or more property of the fluorescent images selected from the group consisting of intensity, area, density, and distribution, comparing the values of the measured property to a known value, and adjusting a parameter of the imaging system as necessary based on the measurement. In a preferred embodiment, the measurements are made of an object or objects identified in the image. In a further preferred embodiment, the parameter is selected from the group consisting of focus quality, accuracy of the stage coordinate system, accuracy of positioning of the objectives, objective offsets, camera skew, stage skew, stage accuracy, system background, sample background, cross-talk background, linearity of the camera response, camera aberrations, camera noise, effective exposure time, shading imperfections, spatial resolution, correct installation of objectives, system magnification, correct installation of filters and dichroic mirrors, signal to noise ratio per optical channel and objective, optical aberrations and artifacts per optical channel and objective, optical transfer function, and pipetting system parameters.

In a preferred embodiment, the test plate comprises a test plate as disclosed above.

As used herein, "adjusting" includes calculating correction factors to compensate for any deficiencies in generated data caused by hardware and software components not performing up to necessary standards, calibrating a component of the fluorescent imaging system to bring it into conformity with specifications, truth samples, veracity checks, or desired ranges; and replacing defective components.

As used herein, a "known value" means a standard of some sort, such as a manufacturer's specification, validated samples, standards generated on a validated system, and standards generated by previous experimentation on the same or a similar instrument.

Thus, the methods of this aspect of the invention provide diagnostic, validation, and calibration tests, as well as methods for standardization or normalization of hardware and software on any type of fluorescence imaging system. The methods of this aspect of the invention involve making measurements of one or more of the fluorescent properties of the microbeads on the plate, such as size, shape, and spatial distribution, as well as the exact position on the test plate at which the objects are imaged (X, Y and Z coordinates), and using the measurements to adjust as necessary one or more of a wide range of fluorescence imaging system parameters to be used for cell-based screening, which enables reproducibility regarding the actual objects being imaged. The methods can also be used to test automated pipetting of fluorescent solutions, as well as accuracy and repeatability of plate handling. The intensity of the microbeads can be used to test whether the overall optical throughput (sensitivity) of the fluorescence imaging system is correct. The spectral properties of the fluorescence emission of the microbeads can be used to test if the correct filters have been installed and are operating correctly. The diameter of the images of the microbeads can be used to test if the correct objectives have been installed properly. The density of the microbeads on the surface tests software applications that identify objects. When the test plate and software are combined with a fluorescent dye solution, the plate can be used to test the functionality of a preprogrammed pipetting system.

For example, intensity of the fluorescent microbeads can be measured in order to calibrate image uniformity by measuring the intensity as a function of position of the fluorescent microbeads, calculating the percentage difference in the intensity values of peripheral fluorescent microbeads in the image relative to the intensity values of the non-peripheral fluorescent microbeads in the image, and normalizing the image intensity of those fluorescent microbeads located at the periphery by utilizing a correction factor calculated from the measurements. Such a correction factor could be determined, for example, by multiplying peripheral image intensities by a factor based on the percentage difference in intensity between the peripheral and non-peripheral microbeads, such that all intensity values are normalized to the intensity values of the non-peripheral fluorescent microbeads. As used herein, the term "peripheral" refers to the external boundary of the image, comprising 5 to 15 percent of the microbeads. The term "non-peripheral" refers to the area of the image not included in the peripheral region.

In another example, the area of the microbeads in pixels is measured in order to verify the correct installation of microscope objectives. Such a diagnostic test could involve comparing the measured area of the microbeads in pixels with the reference area of the microbeads measured on a validated imaging system for one or more objectives installed in the system, and correcting the installation of any objective that yields an incorrect area measurement.

In a further example, the area of the microbeads in pixels is measured in order to calibrate magnification by determining the actual microbead area wherein the calculation is based on the actual microbead diameter and calculating a correction factor wherein the correction factor is the value of the actual microbead area divided by the measured microbead area in pixels.

In another example, microbead fluorescent intensity is measured to verify the correct installation and transmittance properties of filters by measuring the intensity for one or more optical channels of the imaging system, comparing the measured intensity values to the intensity values obtained on a validated imaging system, and replacing filters involved in optical channels for which the measured intensity values do not compare favorably to the intensity values obtained on a validated imaging system.

The method can also be used to calibrate or validate hardware and software for specific cell-based assays that a user might wish to run on a fluorescence imaging system. For example, it is often desirable to analyze translocation of a fluorescent reporter molecule between the cytoplasm and nucleus of an individual cell. The present methods can be used to calibrate a fluorescence imaging system to run such an assay by, for example, using fluorescent microbeads that are similar in size to nuclei (5-10 μm) where the fluorophore is detectable at a first wavelength. The microbeads are imaged in a first channel (i.e.: wavelength) of the fluorescence imaging system. A solution of fluorescent dye that is optically distinguishable from the fluorophore on the fluorescent microbead is added around the microbeads and is analyzed in a second channel. The normalized, or relative intensity is measured (diffuse dye minus the microbead intensity), which mimics measurements that can be made in analyzing translocation between cytoplasm and nucleus in individual cells (the "Nuc trans algorithm) These values can then be used to validate the data derived when carrying out the nuclear translocation assay.

In another example, many cell-based drug screening assays are based on the internalization into the cell of a cell surface receptor. The present methods can be used to validate software used by a fluorescence imaging system to run such an assay by, for example, determining the area, count, and intensity of microbeads 2-5 μm in diameter labeled with a first fluorophore detectable at a first wavelength, and also smaller microbeads to mimic endocytic compartments and intracellular organelles, that are labeled with a second fluorophore that is optically distinguishable from the first fluorophore. These values can then be used to validate the data derived when carrying out the cell surface receptor internalization assay.

In another example, the method can be used to test the functionality, accuracy, and precision of a preprogrammed pipetting system, and to measure the time to collect data after solution addition and the time to fully mix added solution by analyzing the change in fluorescence intensity after pipetting a predetermined volume and concentration of fluorescent solutions onto a fluorescent microbead test plate. A fluorescence imaging system is loaded with a fluorescent microbead test plate in the reader and standard well microplate, containing fluorescent solution, in the pipettor station. The pipetting system is programmed to dispense a fixed amount of fluorescent solution to each of the test wells of the test plate. Baseline images are gathered before and after addition of the fluorescent solution. The images are analyzed with the Nuc trans algorithm that yields the number of objects identified and the average intensity of fluorescence a few pixels beyond the boundary of the objects. See Example 5 for a more detailed description of the pipetting tests.

The invention can be better understood in view of the following examples. These examples are provided for the purpose of illustration only, and should not be construed as limiting.

EXAMPLES

Example 1

Preparation of a Test Plate

A) Reagents

For plate synthesis: Buffer (Dissolve EDAC and NHSS to 5 mM in HBSS (approximately 1 mg/ml)); Falcon Biocoat collagen I 96-well plate; Fluoresbrite, caroboxylate microspheres (10 micrometer diameter BB)

For embedding: Polyurethane Clear Gloss, Home Depot

B) Plate Preparation
1. Calculate the desired number of microbeads per well (10,000 recommended for single density plate, 40,000 per well as highest concentration in 2-fold dilution series).
2. Pipette desired volume from bottle into 15 ml centrifuge tube.
3. Wash microbeads 3× with HBSS.
4. Resuspend microbead into Buffer, at a concentration such that each well gets 100 microliters of microbead suspension (for 20,000 microbeads per well, prepare a 200,000 microbeads/ml suspension).
5. Sonicate microbead suspension.
6. Pipette microbead suspension into each well of 96 well plate.
7. Let microbeads settle by gravity and allow coupling reaction to take place over a 4-hour period.
8. Aspirate Buffer and let plate air-dry overnight. (If desired, plate may be washed in $H_2O$ prior to drying, to remove any remaining salts/coupling reagents.)

C) Embedding
1. Add 10 microliters of polyurethane or other embedding media to each well of air-dried microbead plate. If the polyurethane is too viscous, it can be diluted 1:1 with petroleum ethers and then added to wells in a 10 microliter volume. Acetone-based solvents should not be used, as they will dissolve the microbeads.
2. Air-dry overnight, so that polymerization is complete.

Example 2

Alternate Preparation of a Test Plate

1. Make a 1 mg/mL stock of BSA in 100 mM sodium bicarbonate, pH 8.0-9.0; pipet 100 μL BSA solution into each of the wells of a standard 96-well plate. Mix via slow vortexing with plate adapter or on a rotating platform; incubate plate for at least 1 hour at room temperature.
2. Prepare 'activation buffer': a solution of 50 mM sodium citrate, pH 5.0.
3. Determine stock microbead concentration (Bangs Lab fluorescent green, 10 μm, carboxylate modified): Vortex the stock then count the microbeads (1:50 dilution) via hemocytometer on fluorescence microscope. Stock conc.=Avg # microbeads per square×10,000×50 fold dilution.
4. Vortex stock tube to mix. Pipet the desired volume of microbeads (usually 10,000/well) into 10 mL activation buffer. Can add up to 1 mL microbeads in this 10 mL. Invert to mix, then centrifuge 15 min at 1200×g.
5. Remove the top 8 mL of solution and add 8 mL fresh activation buffer, vortex to mix, then centrifuge 15 min at 1200×g. Preferably the fluorescent microbeads are washed to remove surfactant/detergent.
6. Remove all but 2 mL, resuspend microbeads by vortexing (still in activation buffer); add 20 mg EDAC and 20 mg NHSS to microbeads, rock for 30 minutes.
7. Wash the BSA-coated plate with 20 mM sodium phosphate, pH 7.4-8.0 (3×100 μL per well if by hand), to get rid of any free BSA which can compete for binding to the microbeads.
8. Add 8 mL binding buffer (100 mM sodium phosphate, pH 8.0) to the microbeads, vortex 1 minute to mix, centrifuge as above.
9. Wash microbeads twice with 20 mM sodium phosphate or PBS to remove excess EDAC which can compete with the microbeads for binding sites on the well surface; vortex to resuspend counted microbeads. Adjust concentration to 100,000 microbeads per mL.
10. Sonicate for 5 minutes to avoid clumps and strings of microbeads.
11. Dispense 100 μl/well into 96-well plate (net 10,000 microbeads/well).
12. Centrifuge the plate at 1000×g (approximately 2700 rpm) for 20-30 min.
13. Gently remove solution from wells and allow to dry.
14. Wash wells 3× with water or PBS to get rid of unattached, floating microbeads that interfere with focus.
15. Add aqueous solution and seal the plates with an adhesive or thermal plate seal or alternately add embedding material and dry overnight.

Example 3

Design and Use of a High Content Screening (HCS) Assay to Test Covalent Coupling of Microbeads to the Bottom of Plates A) Assay Design We devised an HCS assay to monitor the covalent coupling of the microbeads to the bottom of the wells. After the microbeads are allowed to settle and attach, the media is aspirated off and the remaining fluid is allowed to air-dry. As the residual fluid film evaporates, tiny droplets begin to form on the bottom surface of the wells, or a large meniscus appears at the edge of the wells. Microbeads that are not attached to the bottom of the wells formed large, multi-microbead aggregates at the edge of the wells and in association with the meniscus or they aggregated into discrete clumps in association with the microdroplets (FIG. 1A). If microbeads are coupled to the bottom of the wells, their disperse distribution is preserved throughout the drying process (FIG. 1B).

B) Testing the Effects of Concentration of Binding Reagent on the Binding of Microbeads Using the microbead aggregation assay described above, we tested the effect of different concentrations of EDAC/NHSS on the covalent coupling of microbeads to collagen coated plates. EDAC and NHSS were dissolved in equimolar ratios to 10 mM concentration, and a 0.5× dilution series was performed across a row of a 96 well plate. Microbeads were allowed to settle in 96 well plates (40,000 microbeads/well) and react for 4 hours, after which the media was aspirated off and the plate allowed to air-dry. Images of microbead lawns were acquired at all concentrations. The data revealed that concentrations of 1.25 mM and above significantly coupled microbeads to the surface of the plate, as revealed by the decrease in microbead aggregate formation.

C) Testing the Composition of the Activation Buffer on the Efficiency of Microbead Binding Different activation buffers were tested for the activation step, including HBSS (Hank's balanced salt solution, which contains 1 mM phosphate buffer, pH 7.4), PBS (contains 10 mM phosphate, pH 7.2-7.6), and 50 mM citrate, pH 5.0. Based on the literature for NHSS and similar chemicals, a lower pH is preferred due to the increased stability of the carboxylate-EDAC-NHS complex at lower pH. Indeed, when microbeads were prepared using these various activation buffers, it was found that the pH 5 buffer produced microbead plates with higher microbead densities than either of the other buffers tested. The presence of salt in the buffer is preferred, however, to reduce adherence of the microbeads to the walls of the vessel in which the coupling is being performed.

D) Testing of Various Chemical Groups for the First Chemical Group of the Surface As an alternative to test plates with collagen as the first chemical group of the surface, other protein substrates were tested for their suitability in providing amine groups for microbead binding. Solutions (in PBS or water) of three different proteins were prepared: bovine serum albumin (BSA), B-D Cell-Tak (a marine protein), and fetal bovine serum (a highly concentrated, ~50 mg/mL, mixture of proteins containing primarily BSA). Twenty microliters of a 7.5% sodium bicarbonate, pH 8.1 solution were added to each well of the test plates followed by 10 μL of the test protein. The test plates comprised one Packard View Plate (polystyrene) and one Whatman glass-bottom plate. The proteins were tested in a two-fold dilution series in the range of 1 mg/mL to 0.125 mg/mL BSA, 0.35 to 0.044 mg/mL Cell-Tak, and 10% to 1.25% v/v in PBS of FBS. The proteins were incubated for one hour, washed, dried, and stored at 4° C. The next day microbeads were prepared according to the alternate protocol given in Example 2 and contacted with the plates. To test the effect of drying on microbead binding, some of the wells were allowed to dry overnight and others were not. The next day the microbead plates were washed gently three times and imaged. The wells containing BSA and FBS had appreciable numbers of microbeads, whereas the Cell-Tak treated wells had very few microbeads. In addition, the wells that were allowed to dry had the greatest number of microbeads, whereas those wells that were washed without drying had very few microbeads remaining.

In a separate experiment, a glass-bottomed plate was coated with either BSA or aminosilane, a non-proteinaceous source of amines. Upon addition of microbeads and imaging as above, the aminosilane-coated wells contained similar numbers of microbeads as the BSA coated wells, however in the case of the aminosilane coated wells it was not necessary to allow the wells to dry; indeed it was preferable to leave the plates wet following centrifugation of the microbeads to the bottom of the wells. However, this procedure was suitable only for glass-bottom plates, as the aminosilane coating procedure did not work on plastic plates.

E) Testing the Effects of Different Microbead Densities on the Formation of Microbead Aggregates We tested the possibility that high microbead plating densities could lead to the formation of microbead aggregates on the surface. Microbeads were suspended in 5 mM EDAC/NHSS in PBS at varying dilutions, and plated at 40,000, 20,000, 10,000 and 5,000 microbeads per well of a 96-well plate. Microbeads were allowed to bond with the surface (bottom of the wells), after which the media was removed and the plate allowed to air dry. At plating densities of 20,000 microbeads/well or greater, the size of the microbead aggregates increases disproportionately with the increase in the number of microbeads. This suggests that microbead aggregation is a function of microbead density at 20,000 microbeads/well or greater, but not at lower densities. On the other hand, we found that both the size and percentage of microbead aggregates at 5,000 and 10,000 microbeads/well was fairly constant, indicating that microbead aggregation is not a problem if the density of the microbeads on the surface is kept below 10,000 microbeads/well. Given that a well of a 96-well plate has a surface area of 0.32 $cm^2$, a surface comprising monodispersed microbeads can be synthesized by plating the microbeads at concentrations lower than 10,000 microbeads/0.32 $cm^2$ or, more generally, approximately 30,000 microbeads/$cm^2$ surface.

F) Testing the Effects of Microbead Rehydration and Fluid Shear Forces on the Attachment of Microbeads to the Plate We tested whether microbeads could be covalently bound to the bottom of the plate, air-dried, and then rehydrated without detaching from the plate. For the experiment, microbeads were left to settle in 5 mM EDAC/NHSS and allowed to react for 4 hours. After the media was aspirated of and the plates allowed to air dry, we rehydrated the microbeads by applying 100 microliters of HBSS into the well, using a 200 microliter pipettor at maximum attainable speed. Nearly 80% of all microbeads remained attached after rehydration in HBSS buffer. In addition, they exhibited much more homogenous fluorescence after they were rehydrated. After the microbeads were rehydrated, we also determined that they could be subjected to vigorous pipetting. Greater than 50% of the microbeads remained attached after we pipetted 100 microliter volumes directly on top of them, and repeated this three times at the maximum attainable pipetting speed with a manual Eppendorf 200 microliter pipettor. The results indicate that the microbead plates can be air-dried for storage and rehydrated, as well as used to test imaging and optics as fluids are pipetted into test plates.

G) Embedding the Microbeads in Inert Polymer Matrix for Mechanical Stabilization and Long Term Storage To stabilize the microbead lawn for long-term storage and to protect against mechanical abrasion, we embedded the air-dried microbead plates in different polymerizable agents. We tested polyurethane (MINWAX™ clear gloss), epoxy (Elmers'™ epoxy resin and hardener, dissolved in acetone), nitrocellulose (fingernail polish enamel), polyacrylate (MINWAX™) and polyvinyl alcohol. After microbeads were covalently attached and air-dried onto 96 well plates, 10 microliters of embedding agent was added to each well. After polymerization was complete, we compared the fluorescent properties of the embedded microbead monolayer with that of air-dried, non-embedded samples. Compared to non-embedded, air-dried microbead monolayers, polyurethane yielded the most comparable result in terms of the fluorescence properties of the microbead monolayer, and did not affect the distribution of the microbeads. Epoxy resin had unfavorable optical properties and the acetone used to dissolve the resin tended to dissolve the microbeads. Polyacrylate did not affect the distribution of the microbeads, but its optical properties were less favorable than those of polyurethane, leading to spatial heterogeneity in microbead fluorescence across the well. Nitrocellulose (fingernail polish enamel) had unfavorable optical properties, and solvents in the enamel tended to dissolve the microbeads. To decrease the viscosity of polyurethane, we dissolved it 1:1 in petroleum ester (NAPTHA) and used the combination as an embedding agent. Microbead lawns thus embedded retained a distribution characteristic of unembedded microbead lawns, yet their optical properties were not as good as when polyurethane alone was used as the embedding agent, but better than the polyacrylate. Finally, when a 20% polyvinylalcohol/5% glycerol mixture in water was used to embed the microbeads, the microbead monolayer proved to be unstable and detached from the bottom of the plate.

H) Comparing the Optical Properties of Air-Dried, Hydrated and Polyurethane/Polyacrylic Embedded Microbeads At higher magnification, we determined that both hydrated fluorescent microbeads and polyurethane or polyacrylic embedded microbeads had more favorable optical properties than air-dried/unembedded microbeads. In the presence of surrounding media, microbeads have homogeneous fluorescence. In air-dried microbead lawns, microbeads exhibit a ring of fluorescence at their periphery and wherever the microbeads touch each other. This ring is likely due to light scattering, produced by differences in the refractive indices between microbeads and air.

I) Testing the Mechanical Stability of Air-Dried and Embedded Microbeads

To test the mechanical stability of air-dried microbeads, the microbead plate was dropped three times from a height of two meters, after which the plate broke. The distribution of microbeads was compared before and after such a mechanical stress. We found that not a single microbead detached, even if the microbeads were not embedded in any polymer matrix. Additional tests revealed that polyurethane or polyacrylate-embedded microbeads were completely stable to manual abrasion with a metal pin.

J) Conclusion

We constructed two types of microbead plates for testing fluorescence imaging systems: Single use (air-dried, rehydratable microbead plates) and multi-use (embedded microbead plates). Unlike other calibration tools, the microbead plates allow complete automation of a variety of diagnostic, calibration, and software validation procedures by making the measurements with established protocols run on fluorescence imaging systems. In order to stabilize microbead deposition, we developed chemical coupling techniques that bind 10 micrometer microbeads to the bottom surface of wells of 96 well plates. After the microbeads are covalently bound to the surface, the plates can be air-dried and stored for long periods of time, without altering microbead distribution or morphology. Air-dried plates can be rehydrated by adding water or buffer. Alternately, the air-dried plates can be embedded under an inert, oxygen-free, airtight polymer coating for indefinite preservation and protection against fluorophore bleaching due to oxygen free radical formation.

Both rehydrated or embedded microbead plates exhibit excellent fluorescent, mechanical and optical properties. To test the stability of the microbead plates, plates have been subjected to large mechanical forces. We demonstrate that the forces needed to dislodge the microbeads are much greater than the forces needed to break the plate. In addition, tests show that microbeads are relatively stable to photobleaching and should provide an easy method to diagnose or calibrate the optics/illumination components of fluorescence imaging systems. Finally, rehydrated microbead plates withstand fluid shear forces associated with manual pipetting, as well as pipetting forces exerted by automated fluid handling systems.

Example 4

Diagnostics, Calibration, and Validation of the Optics, Illumination, Image Analysis Architecture, and Software of a Fluorescence Imaging System A Method to Test the Origin of Stage Coordinate System Problem:

The location of the plate relative to the imaging system is usually not fixed. The origin of the stage relative to the imaging system can be determined using the calibration plate.

Method:

If a well of the calibration plate has beads with sufficient density, or has beads of one color and a uniform film of another color, then a method can be employed to accurately find the edges of the well, and thus infer the location of the well center relative to the stage coordinate system.

This method is only necessary as part of installation of the instrument since the location of the plate within the coordinate system of the stage is fixed and should not vary over time. One approach is as follows:

(1) Allow user to move stage (via software control) until objective is under the appropriate well in the calibration plate. This can be done by providing visual feedback on the display, or by requiring the user to visually observe the objective relative to the well.

(2) Perform image-based auto-focus on the beads so that the beads appear sharp in the image.

Figure 3:
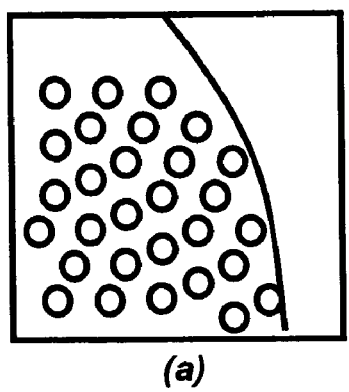
FIG. 3 is an image of well edge using (a) beads of one color and (b) uniform film of another color.
Figure 3:
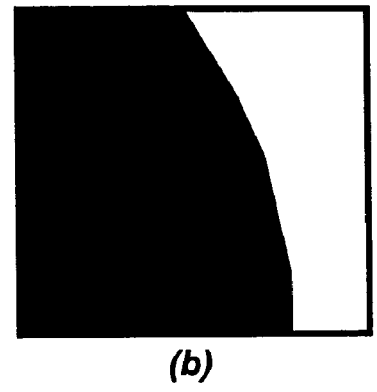

(3) Move stage to the right, one field-of-view at a time, acquiring images until the edge of the well is found. A well edge can be detected by either (a) observing when no beads are detected for a pre-defined distance, or (b) observing a dropoff in intensity in the uniform film. (See FIG. 3).

(4) Obtain an accurate measurement of the location of the well edge by using morphological image-processing operations.

(5) Repeat steps 3 and 4, except moving stage to the left.

Figure 4:
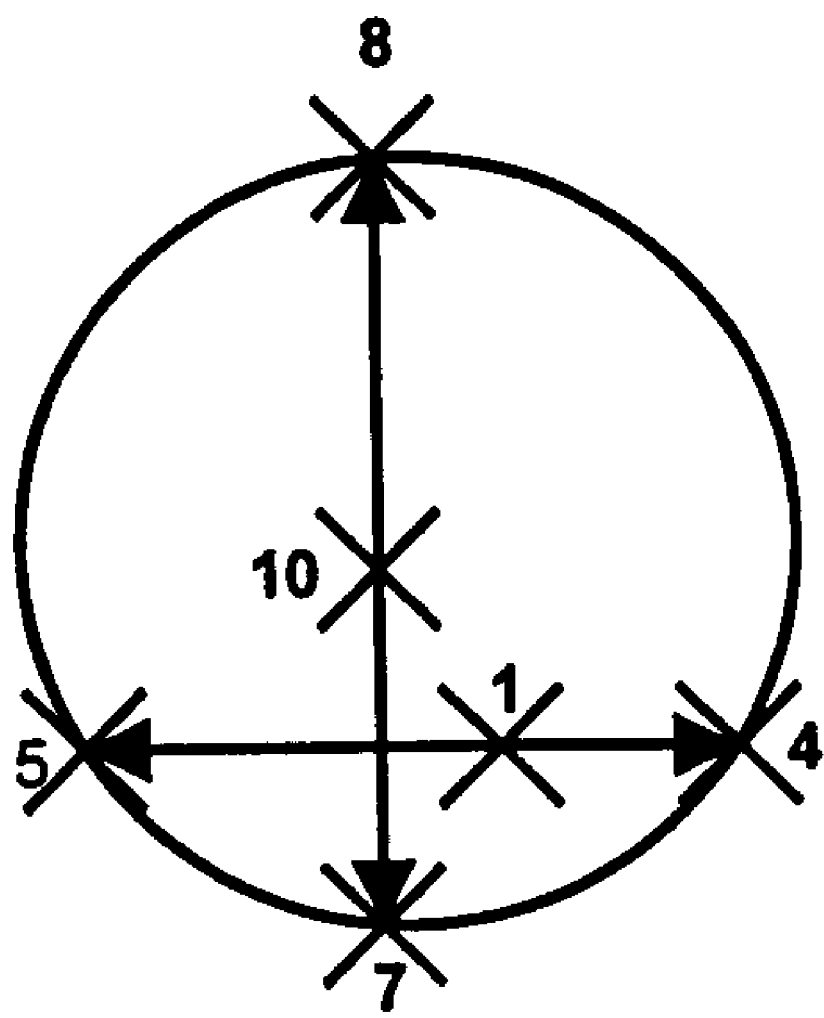
FIG. 4 shows the steps performed to find center of well. (The step numbers correspond to steps defined in the description above.)

(6) Take the midpoint between the two edges (left and right) and define this as the x-center of the well. (FIG. 4)

(7) Repeat steps 3 and 4, except moving the stage down.

(8) Repeat steps 3 and 4, except moving the stage up.

(9) Take the midpoint between the two edges (top and bottom) and define this as the y-center of the well.

(10) Now that the center of the well is accurately determined, the location of the plate relative to the stage coordinates is known.

A Method to Test the Objective Registration (x, y, and z)

Problem:

Due to manufacturing and installation inconsistencies between objectives, a system with automated objectives may suffer from registration problems. Each objective may not be centered at the same location (causing registration problems in x and y) and may have a different focal distance (causing registration problems in z).

Method:

A calibration plate that has a well containing uniform-sized beads could be used to identify the x, y, and z offset per objective. One procedure is as follows:

(1) Move stage to the appropriate well in the calibration plate.

(2) Change to the baseline objective.

(3) Perform image-based auto-focus to find the z position where the beads are in focus.

(4) Record the z position and the focused image for the baseline objective.

(5) Change to the next objective.

(6) Perform image-based auto-focus to find the z position where the beads are in focus. The difference between this z position and the recorded z position for the baseline objective defines the z registration error for this objective.

(7) Move the stage in x or y until it is centered at the same location as the baseline objective. This is accomplished by cross-correlating the current image with that of the stored baseline image (decimate or interpolated). The offset in x and y from the baseline objective defines the x and y registration error for this objective.

(8) Repeat steps 5-7 for each remaining objective.

Once the x, y, and z registration errors are determined for all objectives, this information can be utilized by the software so that: (1) changing objectives will not require performing image-based auto-focus for the new objective, and (2) it would be possible to detect a cell using one objective and then perform measurements using another objective.

A Method to Test the Dye Offsets Per Objective (z)

Problem:

The objectives are designed so that the focal distance is constant for all wavelengths over a given range. However, if a dye emits at a wavelength outside the range that the objective was designed for, the focal distance may be different from that of other dyes.

Method:

Using a calibration plate that has beads of different dyes in the same well, the z offset for each dye can be measured per objective. One procedure is as follows:
  (1) Move to appropriate well in calibration plate.
  (2) Change to a particular objective.
  (3) Configure filters on system in order to image a particular dye.
  (4) Perform image-based auto-focus to find the z position where the beads of the given dye are in focus. Record this z position for this dye/objective combo.
  (5) Repeat steps (2)-(4) for all other objectives and dyes.

This information can then be used by the software so that it could compensate for these z offsets errors. This will reduce the need to perform image-based auto-focus on more than one dye being acquired.

A Method to Test the Camera Orientation/Skew (x and y)

Problem:

The camera may not be oriented perpendicular to the stage travel. Thus a movement of the stage in x may cause the objects that appear in the image to move in both x and y.

Method:

Using a calibration plate containing beads, and taking an image before and after the stage is perturbed in either x or y, the camera orientation/skew can be measured in that direction (x or y). The stage perturbation must be much less than the field of view. To find the direction of skew, the algorithm will cross-correlate the before and after images and then detect the largest peak in the cross-correlation image—the peak corresponds to the direction of skew. This skew value can then be used as a calibration parameter by the software so that the system compensates for this skew during all intra-well movements. During intra-well movements, if the camera orientation is not perpendicular to the stage travel, there is the possibility that there will be overlap between some fields and missed area between others. Thus, it is important to move the stage perpendicular to the camera orientation when it comes to intra-well movements.

A Method to Test the Stage Skew (x and y)

Problem:

The stage may be skewed relative to the plate. Thus, if a plate is organized to have wells that are evenly spaced in both x and y, then moving the stage between adjacent wells would require moving in both x and y rather than just in x or just in y.

Method:

By measuring the location of the center of two wells on the calibration plate, and knowing the spacing between wells on the plate, the stage skew can be determined (in both x and y). The procedure used to measure the location of the center of a well can be the same as the method described earlier to define the origin of the stage coordinate system. This skew can then be used by the software to know how to accurate move well to well. With knowledge of the skew, the accuracy of moving to a specific location within the well would be increased.

A Method to Test the Stage Accuracy (x and y)

Problem:

The stage step size must be determined with high accuracy in order to move the stage from one well on the plate to another with high accuracy. Also, as the stage is used over a long period of time, the stage accuracy may be reduced (due to motor slippage), thus making it desirable to occasionally measure the stage accuracy to verify that the stage is operating properly.

Method:

By moving the stage a predefined amount less than a full field of view, and then measuring how far the beads moved, the stage accuracy can be calculated (in both x and y). For instance, one such procedure is as follows:
  (1) Move to the appropriate well in the calibration plate.
  (2) Perform image-based auto-focus to find the z position where the beads are in focus. Record the focused image.
  (3) Move the stage by N steps in x and y, where N steps is expected to be approximately a fourth of a field-of-view and acquire another image.
  (4) Cross-correlate the two images and find the offset that has the largest cross-correlation coefficient. By knowing the camera resolution, the offset can be translated from pixels to microns.
  (5) The step size (microns/step) can be calculated as follows: x_step_size=x_offset_microns/N, and y_step_size=y_offset_microns/N.

Image Correction

A Method to Test the Pure System Background (Intensity not Related to Sample or Cross-Talk)

Problem:

Images have background intensities due to unintentional stray light that enters the imaging path, and camera and optical deformations.

Method:

Using a blank well on the calibration plate, the background dark field measurement can be made for each dye. This background dark field image (per dye) can then be used to correct all future acquired images (by subtraction of the background image). The procedure to acquire the images would be as follows:
  (1) Move to the well adjacent to the blank well, which contains beads of a single color.
  (2) Perform image-based auto-focus to find the z position where the beads are in focus.
  (3) Move to the blank well without moving the z position.
  (4) Acquire image(s) of background.

A Method to Test the Sample Background (Intensity Derived from the Sample Preparation which are not Due to the Cells)

Problem:

Images have background intensities due to fluorescence of the media, microplate imaging surface, and anything else that is part of the sample preparation that is not directly related to the biological material.

Method:

Measure the intensities of area far from the objects by using the ring intensity feature of the cyt-nuc algorithm. The ring needs to be made sufficiently large such that the ring does not capture intensities generated by the bead.

A Method to Test the Cross-Talk Background

Problem:

Overlap of excitation and emission spectra of the dyes and the filter sets can cause cross-talk between optical channels. As a result, the image acquired in one channel will actually contain a small additive contribution from the signal in each of the other channels. Thus, it is desired to be able to automatically remove the cross-talk contribution to each channel to make them independent of one another.

A variation of this topic is where a particular dye will appear in multiple channels. The only way to distinguish these multi-colored (combinatorial) probes from the single-color probes is by utilizing knowledge about how much cross-talk each dye produces. For the case of the single-colored probes, the cross-talk will usually be small, while the cross-talk for the combinatorial probes will usually be larger. Thus, it would be possible, for instance, to extract three probes out of two channels if the amount of cross-talk per dye is known.

Method:

Observing the cross-talk between channels using beads of different dyes can be used to determine the amount of cross-talk between each channel. This information can then be used to correct for cross-talk in all future images acquired. One such procedure is as follows:

(1) Move to appropriate well on calibration plate that has beads of a single color (dye).
(2) Perform image-based auto-focus to find the z position where the beads are in focus. Record this image.
(3) Acquire images for each channel, where a channel corresponds to the filter combination that is used to image a particular dye.
(4) Identify the beads in the original image.
(5) Compare the average intensity of the beads in the original image with the average intensity of the beads in the other channels. Normalize these values by dividing by the average intensity of the beads in the original image.
(6) Repeat for all channels (dyes), producing, for example, the following table:

TABLE 1

|  | Channel 1 | Channel 2 | Channel 3 | Channel 4 |
|---|---|---|---|---|
| Dye 1 beads | 1.00 | 0.1 | 0.2 | 0.3 |
| Dye 2 beads | 0.2 | 1 | 0.3 | 0.1 |
| Dye 3 beads | 0.3 | 0.1 | 1 | 0.1 |
| Dye 4 beads | 0.1 | 0.2 | 0.1 | 1 |

The procedure to calibrate the images using these numbers is as follows, given cells that were labeled with two dyes, 1 and 3:

(1) Acquire an image in channels 1 and 3 of the cells.
(2) Create a matrix, A, which contains a subset of the above table as follows:

TABLE 2

|  | Channel 1 | Channel 3 |
|---|---|---|
| Dye 1 beads | 1.00 | 0.2 |
| Dye 3 beads | 0.3 | 1.00 |

(3) Transpose A and calculate the inverse, producing the matrix B.
(4) Correct the channel images (1 and 3) by performing the following calculation on each pixel: $[\text{dye1 } \text{dye2}]^T = B * [\text{ch1 } \text{ch2}]^T$.

A Method to Test the Linearity of Camera Response

Problem:

Not all cameras produce a linear response in gray-levels. If the gray-levels are linear, then doubling the exposure time should also double the gray-level of each object pixel.

Method:

Using the calibration plate, acquire images of the beads using two or more exposure times. Each bead should produce a range of gray-levels. By increasing the exposure time by a certain percentage, the gray-level of each object pixel should also increase by that same percentage. Thus, the linearity of the gray-levels can be measured by observing individual pixels, or by analyzing a histogram of the entire image.

A Method to Test the Camera Aberrations (Hot/Cold Pixels, Shutter Failure)

Problem:

Camera problems can drastically affect the output of an HCS system. The most common issues are hot/cold pixels, and shutter failures. Shutter failures typically appear either as a barn door (part of image is darker than the rest) or the image is blurred in a single direction.

Method:

The camera aberrations can be measured by evaluating images of the beads. Barn door shutter failures can be detected by observing how the histogram changes across the columns (or rows) of the image. Shutter failures that caused a blurred image in a single direction can be detected by comparing the correlation coefficient of the image correlated with a shifted version of itself in the x and in the y directions—if there is no blurring, the coefficients will be equal.

A Method to Test the Camera Noise

Problem:

Camera noise contributes to the quality of the measurements made by the system. Camera noise is a function of gray-level of the signal.

Method:

Since the beads produce a wide range of gray-levels, acquiring images of the same beads numerous times over a short period of time, will quantify the camera noise per gray-level.

A Method to Test the Effective Exposure Time

Problem:

The speed and latency of the shutter(s) will affect the actual exposure time.

Method:

It is expected that altering the exposure time by a certain percentage will cause the measured intensity values of the beads to change by the same percentage. Thus, by acquiring several images of the beads using three or more exposure times, the effective exposure time can be measured. The difference between the requested exposure time and the effective exposure time is the exposure time error. If this error is known a priori, then this error can be compensated for during operation of the system.

Optical Quality

A Method to Test Shading Imperfections in the Images (Per Dye)

Problem:

Shading imperfections arise from a number of sources. The potential sources are, the illumination not being uniform across the entire field of view, and the objective turret or dichroic mirror housing not being positioned properly. These imperfections cause the intensity of a given bead to vary as a function of location within the image.

Method:

Move the stage around and acquire images of the bead(s) such that the same bead(s) traverse all (or most) portions of the image. This will produce a map of shading imperfections across the image. This information about the illumination pattern can be used to calibrate all future images acquired by dividing the acquired image with this illumination pattern. Alternatively, this information can be used to verify that the light source is producing a relatively flat illumination pattern. Note that this procedure must be applied to all relevant dyes since the illumination pattern is dependent on the dye.

A non-limiting example of such a method, and results one might obtain, is as follows:
1. Bead intensities are measured as a function of position in the image.
2. Calculations using the intensities show that beads positioned in the outer 10% of the image are 5% dimmer than beads positioned within the inner 90% of the image.
3. Intensities measured in the outer 10% of the image are multiplied by 1.05 to correct for the intensity decrease that is produced by the system at the outer portion of the image.

Spatial Resolution

Problem:

The spatial resolution of the optical system impacts the image quality.

Method:

The ideal profile of a bead can be determined mathematically. However, the observed profile may vary from the expected (ideal) profile because of the spatial resolution of the optics. By comparing the observed profile with the expected profile, the spatial resolution of the optics can be inferred.

A Method to Test the Installation of Objectives and Calibrate the Magnifications of the System for Each Objective Problem:

Objectives of different magnification are installed on most microscopes by the manufacturer or user. Many modern microscopes force the user to select the desired objective via a remote control device. Thus, visual verification of the proper selection of an objective by looking at the objective (not the image) is no longer common. Also, when object sizes are measured by a fluorescence imaging system, the magnification power must be calibrated.

Method:

The correct installation of objectives in a microscope can be tested by measuring the sizes of microbeads, which should be in the range of 2.0-10 microns in diameter, with all of the objectives installed on the imaging system. The measured area of a bead should follow the square of the magnifying power of the objective. This can be seen by considering the following:
1. The observed diameter of the image of a bead is directly proportional to the magnifying power of the objective. Therefore if the objective magnifying power doubles then the observed diameter doubles.
2. The area of the image of a bead is dependent on the diameter by the following area equation:

$$\text{Area} = \pi \times (\text{diameter}/2)^2 \text{ (this is the area of a circle)}$$

Thus, if the observed diameter doubles, because the magnifying power doubles, then the observed area increase by a factor of $2^2=4$.

For example if the area of a bead measures 30 pixels on a CCD camera chip integrated into a fluorescence imaging system that uses a 5× objective, then the area should measure 120 pixels with a 10× objective and 480 pixels with a 20× objective. To test for the correct installation of objectives, the user compares the measured area of the beads with the reference areas determined on a validated fluorescence imaging system. If the results are 30, 120, and 120 pixels, the user would quickly determine that the system was set up with a 5×, and two 10× objectives instead of the desired set of 5×, 10×, and 20× objectives.

To calibrate the magnification of the fluorescence imaging system, the measured sizes of the previous example (30, 120, and 480 pixels) would be used in the following equation, $$\text{calibrationfactor} = (\text{actual bead area})/(\text{measured bead area})$$

where actual bead area is calculated from the diameter provided by the bead manufacturer, and the units of the measured bead area is pixels.

Thus, in our examples, if the actual bead area as provided by the manufacturer is 20 square microns, then the calibration factors would be:

30/20=1.5 square microns per pixel for the 5× objective,
120/20=6.0 square microns per pixel for the 10× objective, and
480/20=24 square microns per pixel for the 20× objective.

Method to Test the Installation of the Filters and to Test the Transmittance Properties of Each Optical Channel Problem:

A typical fluorescence microscope is installed with 2-8 excitation filters, 2-8 emission filters, and 2-4 dichroic mirrors. Each optical channel is comprised of 1 excitation filter (also called an exciter), 1 emission filter (also called an emitter) and 1 dichroic mirror (also called a dichroic). It is common for filter installers to make mistakes when installing many filters and mirrors on a sizable fluorescence imaging system. A method to test for correct installation of filters would be very useful.

Specific transmittance properties of each filter and mirror are important to create a high quality optical channel that is used for imaging (exciter, emitter, and dichroic mirror are combined for one channel). A method to measure the performance of typical optical channels would again be very useful. If a channel shows poor performance, then one wants to quickly identify which of the three elements of the channel is causing the poor performance. Such poor performance can be caused by filter manufacturing defects, use of an optical element wear physical deterioration of a filter as a function of use and time or improper use/cleaning.

One Color Bead Plate

If a population of one color beads:
(a) absorbs light over the wavelength range passed by the exciters,
(b) emits light over the wavelength ranges passed by the dichroic mirrors and emitters, and (c) has absorbance and emission spectra that are single peaked, 1) then this population of one color beads can be used to test for correct installation of exciters, emitters, and dichroics. (Single beads that have the range necessary for a four channel imaging system are not common, but may become common in the future; the solution to this broad range problem is discussed in the next section entitled, "Two color bead plate"). The fluorescent microbeads are imaged, and the intensities of the fluorescent microbeads are measured with every combination of exciter, emitter, and dichroic on the fluorescence imaging system. (Those skilled in the art will know that measuring the background intensity of the image adds valuable information related to filter performance, but that background measurements are excluded here for brevity.) The measured bead intensities are compared to ranges of values of bead intensities obtained on a validated fluorescence imaging system.

The ranges of values of bead intensities are obtained by the following method:

2) Validate 20 sets of parts that will be used to assemble 20 imaging systems identical to the imaging system that will be tested with the test plate. The validation of the 400 parts must be on test stations that are independent of the imaging system; those skilled in the art will know that the number 20 could be changed to as few as 3 or as great as 50 (the selection of this number influences the statistical confidence the test designer has in the reference ranges).

3) Assemble the 20 imaging systems.

4) Validate the assembly by eye inspection of all assembly steps, and by measuring system functions with a microplate filled with 100 ul of quinine sulfate in each well; quinine sulfate (a) is fluorescent, (b) emits light over the range 370-500 nm, and (c) is Standard Reference Material 936a of the National Institute of Standards & Technology (NIST). It is important to have a test material that is independent of the current microbead-based test plate.

5) Put the test plate on all 20 systems. Image the fluorescent microbeads, and measure the intensities of the fluorescent microbeads with every combination of exciter, emitter, and dichroic on the fluorescence imaging system. Those skilled in the art will know that measuring the background intensity of the image adds valuable information related to filter performance, but that background measurements are excluded here for brevity.

6) Calculate the average of the 20 intensities that result from the 20 tests of every of exciter, emitter, and dichroic on each fluorescence imaging system.

7) The passing range is: average±(0.05 times the average). Those skilled in the art will know that this ±5% deviation from the average may have to be reduced or increased as the requirements of the imaging system change with the biological applications; some applications will allow greater than 5% deviation while others will require less than 5% deviation. Those skilled in the art will know that the acceptable range must be evaluated for every application.

Below are 3 hypothetical examples of cases where some of the optical channels fail, and where the tester can quickly determine which optical elements caused the failures. The imaging system in these examples is based on combinations of 3 exciters, and 3 dichroic-emitter pairs (a dichroic-emitter pair is a combination of a dichroic mirror and an emission filter). The combinations of exciters with a dichroic-emitter pairs results in 9 optical channels.

Example 1

Exciter a has Failing Performance and Needs to be Replaced

TABLE 3

|  | Exciter A | Exciter B | Exciter C |
| --- | --- | --- | --- |
| Dichroic emitter pair X | Ch. 1 Fails | Ch. 4 Passes | Ch. 7 Passes |
| Dichroic emitter pair Y | Ch. 2 Fails | Ch. 5 Passes | Ch. 8 Passes |
| Dichroic emitter pair Z | Ch. 3 Fails | Ch. 6 Passes | Ch. 9 Passes |

Example 2

Exciter A and Exciter B were Switched by Installers, and Thus their Positions in the Imaging System Need to be Reversed

TABLE 4

|  | Exciter A | Exciter B | Exciter C |
| --- | --- | --- | --- |
| Dichroic emitter pair X | Ch. 1 Fails | Ch. 4 Fails | Ch. 7 Passes |
| Dichroic emitter pair Y | Ch. 2 Fails | Ch. 5 Fails | Ch. 8 Passes |
| Dichroic emitter pair Z | Ch. 3 Fails | Ch. 6 Fails | Ch. 9 Passes |

Example 3

Dichroic Emitter Pair X has Failing Performance, and Thus the Pair Needs to be Replaced with a Pair that Yields Passing Test Results

TABLE 5

|  | Exciter A | Exciter B | Exciter C |
| --- | --- | --- | --- |
| Dichroic emitter pair X | Ch. 1 Fails | Ch. 4 Fails | Ch. 7 Fails |
| Dichroic emitter pair Y | Ch. 2 Passes | Ch. 5 Passes | Ch. 8 Passes |
| Dichroic emitter pair Z | Ch. 3 Passes | Ch. 6 Passes | Ch. 9 Passes |

Two (or More) Color Microbead Plate

As discussed in the previous paragraph the fluorescent microbeads need to absorb light over the wavelength ranges passed by the exciters, and emit light over the wavelength ranges passed by the dichroic mirrors and emitters. If a one color fluorescent microbead does not satisfy these criteria, then two or more different color fluorescent microbeads need to be present in the same field. For example if the exciters, dichroics, and emitters, pass light over the range 350-700 nm, but fluorescent microbead population 1 only absorbs and emits light over the range 350-500 nm, then fluorescent microbead population 2 needs to absorb and emit light over the range 500-700 nm. Similarly if fluorescent microbead population 1 works over the range 350-450 nm, fluorescent microbead population 2 works over the range 450-600 nm, then a third fluorescent microbead population is needed to work over the range 600-700 nm. The extension to 4, 5, 6 etc. color fluorescent microbead plates is apparent to one skilled in the art.

A Method to Test the SNR (Per Dye and Objective)

Problem:

The signal to noise ratio of the images will vary depending on the quality of the optics and the quality of the camera. This image noise is derived from (a) noise in the camera and (b) noise in the excitation light. Camera noise is derived from dark current produced by the CCD chip, readout noise as charge on the CCD chip is converted into electrical signal, and other sources. Signal to noise ratios are very important because the noise set a lower limit on the level of the signal you can use to derive valuable information.

Method:

Pixel values in an image are actually just standard electrical signals that are usually presented in an image display. Measuring signal and noise in electrical signals is a standard procedure. For example, by creating a fluorescent microbead mask and defining a large ring-shaped region around the mask by dilating the fluorescent microbead mask, the fluorescent signal from the fluorescent microbeads (bead mask) and the background signal (non-mask) can be obtained. Any other imaging assay that segments the image into two domains can be used (i.e.: one domain with fluorescent microbeads, and one without). The ratio of the average fluorescent signal of the fluorescent microbeads to the standard deviation of the fluorescent signal of the fluorescent microbeads is the signal to noise ratio for the system. The ratio of the average fluorescent signal of the fluorescent microbeads to the average fluorescent signal of the ring shaped region around the fluorescent microbeads is the signal to background value.

A Method to Test for Optical Aberrations and Artifacts (Per Objective, Dye)

Problem:

There are many known optical aberrations and artifacts that can be measured. Each of these aberrations and artifacts can adversely affect the measurements made with a fluorescence imaging system.

Method:

By imaging the beads, the detection of aberrations and artifacts can be performed. If any occur, then this should be used as an indicator that the system is out-of-spec.

A Method to Test Image-Based Auto-Focus

Figure 5:
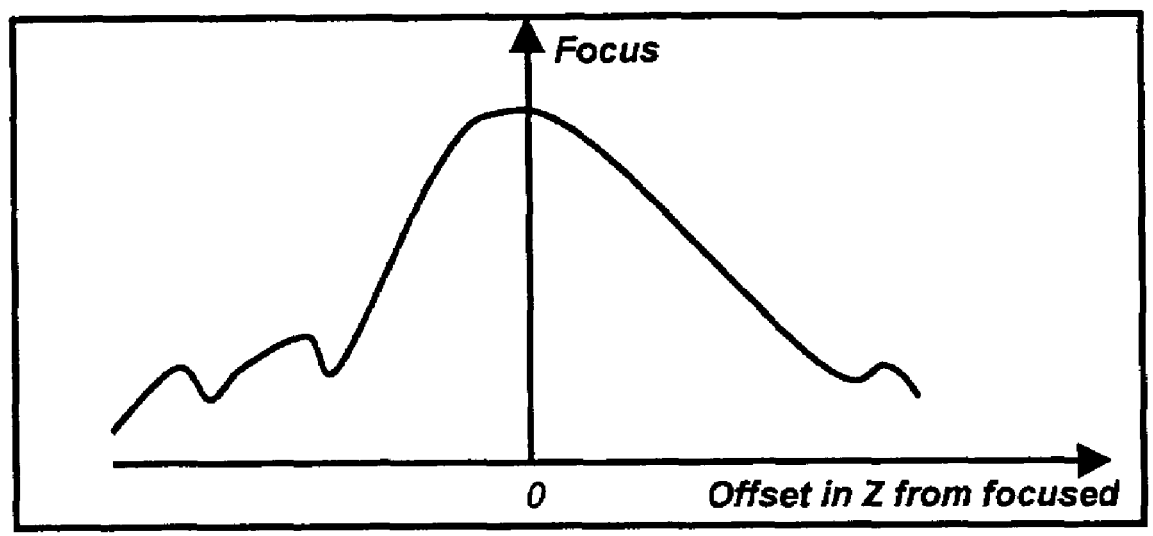
FIG. 5 shows an example Focus score curve

Problem:

The image-based auto-focus algorithm determines the best focus position by calculating a metric on each image, and the image that has the largest score is considered the best focus. As the objective is moved away from the best focus position, the score is reduced. This focus score is usually a measure of the image contrast. The ability for the focus metric to accurately determine focus is dependent on how this score is altered as the objective is moved away from the best focus position. An example focus score curve is shown in FIG. 5.

The shape of the focus score curve is dependent not only on the content of the field, but also on (1) the optical transfer function of the system, and (2) optical aberrations or artifacts that appear focused in other focal planes other than that of the sample. These two factors could (a) alter the flatness of the focus score curve, (b) shift the location of the peak, and (c) create additional "false" peaks.

By measuring the focus score curve of a plane of beads, the auto-focus algorithm can be calibrated for the particular instrument. The parameters that can be calibrated in a typical auto-focus algorithm are:

(a) z step size of the search, (b) z offset from the observed peak, and (c) the interpolation method used to fine-tune the search.

The use of beads as the sample for this test is very useful since the height and shape of the beads is known and has little variability. If the sample being auto-focused is of a different height and shape than the beads, and the expected height and shape are known, the auto-focus algorithm can adjust the calibration parameters accordingly.

Assay Verification

1. Application software for analyzing specific cell-based assays can be tested with known input images derived from well-controlled calibration plates. Assays can be calibrated for proper scaling; problems with software parameters can be diagnosed; and the accuracy and reproducibility of output data can be verified with defined, truth images derived from calibration plates. The plates containing beads and fluorescent films in various preparations can be used to test the following assays:

2. Nuclear Translocation: Beads the same size as nuclei (5-10 um) are imaged in channel 1. Diffuse fluorophore of a different color is added around the beads and is analyzed in channel 2. The normalized, or relative intensity is measured (diffuse dye minus the bead intensity). Wells with various, known concentrations of fluorophore can be used to calibrate the linearity of the assay output. The measured size of the nuclei can be verified with beads of defined diameter.

3. Viability: Counts of nuclei and cytoplasm can be made with beads and diffuse fluorescent dye as with Nuc trans.

4. Spreading: The size of beads (5-10 um) can be measured in channel 1 and 2 (set to the same color). The size of the beads can be measured. Islands of polymer surrounding attached beads containing different concentrations of fluorophore can be analyzed for the assay sensitivity to variable cell body fluorescence intensity.

5. Receptor internalization: The area, count and intensity of beads (2-5 um) can be counted. Small beads of one color (to mimic endocytic compartments and intracellular organelles) could be mixed with large beads of a different color (to mimic nuclei). Islands of fluorescent polymer film containing small beads surrounding larger, attached beads can be used to model whole cell bodies with substructures.

6. Cytotoxicity: Similar to Receptor Internalization. Small beads of multiple colors can be used for the multiple channels of cytotoxicity.

7. Cytoplasm to Membrane Translocation: Beads that have whole volume dye labeling can be additionally labeled on the surface with second fluorophore. The cytomem application could be calibrated with this model for cells labeled throughout the cytoplasm vs. cells labeled only at the membrane. This is a unique use of the three-dimensionality of the beads to calibrate an assay that can distinguish surface vs. volume of tall objects.

System to System Variation

Once a reference fluorescent microbead plate with known characteristics has been identified, it is possible to determine instrument-to-instrument variations. Measurement of the fluorescent intensity of the microbeads with an integration time that is constant and depends on the fluorescent channel provides a metric with which to compare instruments. Collection of intensity data for instruments that have been completely calibrated and validated provides a distribution of expected values. After a pattern has been developed, instruments can be built so that the calibrating measurements are within a certain range of such expected values.

Day to Day Variations

Day to day variations can be accounted for if the fluorescent microbead plate were scanned prior to each assay run and modifications made to instrument parameters.

Example 5

Testing a Pipettor System

A Method to Test the Pipetting System

A fluorescent microbead plate calibration assay was developed to test (1) the time to collect data after solution addition, (2) the time to fully mix added solution (defined as the "complete mixing time"), and (3) pipettor accuracy, based on the change in fluorescence intensity after pipetting a predetermined volume and concentration of fluorescent solutions onto a fluorescent microbead plate.

The two times (1 and 2 above) were tested on a pipetting system. The methods, pass/fail criteria, test results, and conclusions follow. A fluorescence imaging system was hand loaded with a fluorescent microbead plate in the reader, and a Costar 96 well microplate in the pipettor station. The fluorescent microbead plate contained PolySciences blue-emitting (blue channel) carboxylated beads which were chemically cross-linked to the collagen coated wells. The fluorescent microbead plate test wells received 200 µl of Hanks Buffered Saline Solution (HBSS). The Costar 96 well plate received 200 µl of 250 uM fluorescein in matching test wells. The system was programmed to add 40 µl of the fluorescein at 100 µl per second, 20 mm above the bottom of the test well. Baseline images were gathered approximately 60 and 30 seconds before addition of the fluorescein. The images were analyzed with the cyt-nuc algorithm that yields the number of objects identified, and the average intensity of fluorescence a few pixels beyond the boundary of the objects ("average ring intensity"), as discussed above. Images were 12 bit, and therefore the maximum possible value for average ring intensity was 4095. Other algorithms can also be used, such as measuring all non-bead fluorescence, which would yield similar results as a measurement of the ring fluorescence.

On the nuclear (blue channel) channel, individual fluorescent microbeads and fluorescent microbead aggregates were correctly identified by the algorithm. Before and after pipetting, the images remained in register and the beads withstood fluid shear forces associated with the pipetting action, as revealed by the position of the imaged beads on the field.

On the cytoplasmic (FITC) channel, the average ring intensity increased approximately 30-fold upon addition of fluorescein solution. The signal remained constant after the addition for the full 60 seconds of the experiment. The first ring value (e.g.: intensity of a ring around the bead (as defined by cyt-nuc algorithm)) was produced 19 seconds after the addition of the fluorescein, and subsequent ring values were the same (within acceptable noise) as the first value. Thus (1) the time to collect data after solution addition is 19 sec, and (2) the complete mixing time was less than 19 seconds. The maximum observed ring value was 3850.

The pass/fail criteria for (1) the time to collect data after solution addition, and (2) the complete mixing time is determined as follows. These two times (1 and 2 above) must be much less than the time it takes for a biological response to be 50% complete. An example is the internalization of receptors after a stimulant binds to the surface of a cell. The internalization process varies for different cell types, stimulants, and experimental conditions but those skilled in the art will accept 2-10 minutes as a reasonable guess for the time it takes the internalization process of a typical cell under typical laboratory conditions to be 50% complete. Thus solution mixing must be complete in much less than two minutes on a pipetting system that will measure receptor internalization on typical cell line under typical laboratory conditions. In the present example (example 5) the mixing is complete in less than 19 seconds and thus the tested pipetting system passes the test for mixing time for use with a receptor internalization assay. Those skilled in the art will see that it also passes the test for mixing time for many other biological assays that are used in biological research and drug discovery laboratories. Similarly it also passes the test for the "time to collect data after solution addition".

The pipettor accuracy (test 3 presented above) can be measured in a very similar way to the tests just presented to test the two times (1 and 2 above). Fluorescence intensity is linearly proportional to fluorophore concentration. Therefore if a pipetting system adds solutions that results in the doubling of the fluorophore concentration, then the measured intensity doubles as well. One example of a method to measure pipettor accuracy is as follows:

1. Put 100 ul of a thoroughly mixed mixture of working fluorescent solution into a well of a 96-well microplate
2. Measure the intensity of the solution with the method described in the tests 1 and 2 presented in this example 5 of pipetting tests.
3. Use the pipettor to add 10 ul of the same working solution to the wells and thoroughly mix.
4. Measure the intensity.
5. Repeat steps 3 and 4 nine times.
6. Calculate the percent change in intensity after each addition.
7. Pass or Fail the pipetting system based upon the following reference standards: The first change should result in intensity increase of $(10\pm2)/110\%$ for the first addition, the second $(10\pm2)/120\%$, the third $(10\pm2)/130\%$ etc. The accuracy of the pipetting system passes if all changes fall within these predicted ranges. Note: a range of $\pm 2$ ul in an experiment where the well volume is $\geq 100$ ul is acceptable because 10% is total error tolerated in most biological experiments; in the present example the pipetting system contributes no more than 2% error.

Those skilled in the art will see that the test can be made more rigorous by including more than just the 10 ul additions (one could repeat the test with 20 ul additions, 30 ul, etc. additions).

We claim:

1. A method for testing a fluorescence imaging system comprising:
   a) providing a test plate comprising
      i) a surface comprising at least a first chemical group for binding;
      ii) fluorescent microbeads, wherein the fluorescent microbeads comprise at least a second chemical group that is covalently bound to the at least first chemical group on the surface; and
      iii) a polymeric layer in which the fluorescent microbeads are embedded;
   b) acquiring fluorescent images from the fluorescent microbeads;
   c) making a measurement of a property of the fluorescent images selected from the group consisting of: intensity, area, density, and distribution;
   d) comparing the values of the measured property to a known value; and e) adjusting a parameter of the fluorescence imaging system as necessary based on the values of the measured property.

2. The method of claim 1 wherein the polymeric layer comprises a polymer selected from the group consisting of polyurethane, polyacrylate, polysilicones, polyglycols, and polyvinyl alcohol.

3. The method of claim 1 wherein the at least first chemical group and the at least second chemical group are covalently coupled.

4. The method of claim 1 wherein the at least first chemical group comprises a reactive amine group.

5. The method of claim 1 wherein the at least first chemical group comprising a reactive amine group is selected from the group consisting of collagen I, bovine serum albumin, fibronectin, laminin, fragments thereof, and organosilanes.

6. The method of claim 1 wherein the at least second chemical group comprises a chemical group selected from the group consisting of carboxylate groups, amide groups, or sulfhydryl groups.

7. The method of claim 1 wherein the at least second chemical group comprises a carboxylate group.

8. The method of claim 1 wherein the fluorescent microbeads further comprise at least a third chemical group.

9. The method of claim 1 wherein the polymeric layer is doped with a fluorophore that is optically distinguishable from the fluorescent microbead.

10. The method of claim 1 wherein the fluorescent microbeads comprise fluorescent microbeads of different sizes.

11. The method of claim 1 wherein the fluorescent microbeads comprise fluorescent microbeads of uniform size.

12. The method of claim 1 wherein the fluorescent microbeads in total comprise two or more fluorophores, and where the two or more fluorophores are optically distinguishable.

13. The method of claim 1 wherein the polymer layer comprises a series of polymer islands.

14. The method of claim 1 wherein the surface comprises wells and wherein the fluorescent microbeads are located within the wells.

15. The method of claim 14 wherein the fluorescent microbeads are monodispersed in the well.

16. The method of claim 1 wherein the measurements are made of an object or objects identified in the image.

17. The method of claim 1 wherein the parameter is selected from the group consisting of focus quality, accuracy of the stage coordinate system, accuracy of positioning of the objectives, objective offsets, camera skew, stage skew, stage accuracy, system background, sample background, cross-talk background, linearity of the camera response, camera aberrations, camera noise, effective exposure time, shading imperfections, spatial resolution, correct installation of objectives, system magnification, correct installation of filters and dichroic mirrors, signal to noise ratio per optical channel and objective, optical aberrations and artifacts per optical channel and objective, optical transfer function, and pipetting system parameters.

18. The method of claim 1 wherein the adjusting comprises one or more of calculating correction factors to compensate for any deficiencies in generated data caused by hardware or software components not performing up to necessary standards, calibrating a component of the fluorescent imaging system to bring it into conformity with specifications, truth samples, veracity checks, and replacing defective components.

19. The method of claim 1 wherein the method is used to provide one or more of diagnostic tests, validation tests, calibration tests, hardware standardization, hardware normalization, software standardization, and software normalization.

* * * * *